United States Patent [19]

Osei-Gyimah et al.

[11] Patent Number: 5,091,399
[45] Date of Patent: Feb. 25, 1992

[54] ANTIMICROBIAL COMPOUNDS AND METHODS OF USE

[75] Inventors: Peter Osei-Gyimah, Horsham, Pa.; Samuel E. Sherba, Willingboro, N.J.

[73] Assignee: Rohm and Haas Company, Philadelphia, Pa.

[21] Appl. No.: 625,284

[22] Filed: Dec. 10, 1990

[51] Int. Cl.⁵ .............. C07D 417/12; A61K 31/425
[52] U.S. Cl. .................................. 514/367; 548/171
[58] Field of Search ....................... 548/171; 514/367

[56] References Cited

U.S. PATENT DOCUMENTS

| | | | |
|---|---|---|---|
| 3,546,235 | 12/1970 | Bader et al. | 260/299.8 |
| 3,712,908 | 1/1973 | Bader et al. | 260/327 |
| 3,914,301 | 10/1975 | Miller et al. | 424/270 |
| 4,310,590 | 1/1982 | Petigara | 260/561 |

FOREIGN PATENT DOCUMENTS 7012156  5/1970  Japan ................... 548/171

*Primary Examiner*—Robert Gerstl
*Attorney, Agent, or Firm*—Michael B. Fein

[57] ABSTRACT

Compound having antimicrobial activity having the formula

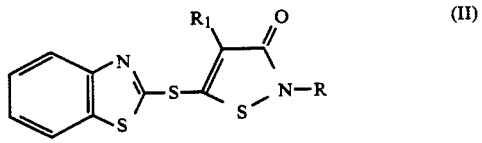

(II)

wherein

R is $(C_1-C_{18})$alkyl, $(C_3-C_8)$cycloalkyl, $(C_6-C_{18})$aryl, $(C_7-C_{18})$aralkyl, or $(C_7-C_{18})$alkaryl, provided that aryl or the aryl portion of said aralkyl or alkaryl are optionally substituted with halo or methyl; and $R_1$ is H, Cl or methyl and method for inhibiting growth of microorganisms using said compound.

13 Claims, No Drawings

ANTIMICROBIAL COMPOUNDS AND METHODS OF USE

BACKGROUND OF THE INVENTION

1. Field of the Invention

This invention relates to novel compounds having biocidal activity and their use as antimicrobials.

2. Description of the Prior Art

A. U.S. Pat. No. 3,546,235 (1970) and U.S. Pat. No. 3,712,908 (1973), assigned to Ciba-Geigy Corporation, disclose that 5-chloro-1,2-dithiol-3-one reacts with metal salts of thiols by nucleophilic substitution to give 5-substituted sulfides, unaccompanied by ring-opening. For example, 4,5-dichloro-1,2-dithiol-3-one reacted with sodium 2-mercaptobenzothizole to give compound of Formula I.

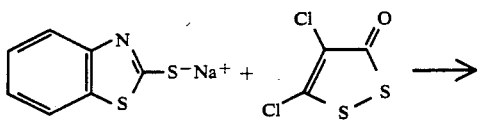

I

B. U.S. Pat. No. 3,914,301 (1975), assigned to Rohm & Haas Co., discloses that isothiazolone systems undergo ring-opening with nucleophiles such as mercaptans to give acrylamide derivatives.

U.S. Pat. No. 4,310,590, also assigned to Rohm and Haas Co., discloses 3-isothiazolones substituted with cyano, piperidino, thiocarbamoylthio, and the like.

SUMMARY OF THE INVENTION

It is an object of the present invention to provide novel compounds having improved antimicrobial activity.

Another object is to provide new methods for inhibiting growth of bacteria, fungi, algae, and the like.

These objects and others as will become apparent from the following disclosure are achieved by the present invention which comprises in one aspect compounds having antimicrobial activity having the formula

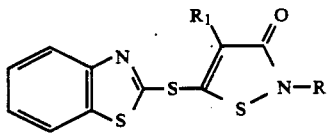

wherein
R is $(C_1-C_{18})$alkyl, $(C_3-C_8)$cycloalkyl, $(C_6-C_{18})$aryl, $(C_7-C_{18})$aralkyl, or $(C_7-C_{18})$alkaryl, provided that aryl or the aryl portion of said aralkyl or alkaryl are optionally substituted with halo or methyl; and
$R_1$ is H, Cl or methyl.

In another aspect the invention comprises a method for inhibiting the growth of bacteria, fungi, or algae which comprises incorporating into or onto a locus subject to contamination an effective amount of said compound, optionally with an agronomically acceptable carrier.

DETAILED DESCRIPTION OF THE INVENTION AND THE PREFERRED EMBODIMENTS

The compounds of the invention have the formula (II)

wherein
R is $(C_1-C_{18})$alkyl, $(C_3-C_8)$cycloalkyl, $(C_6-C_{18})$aryl, $(C_7-C_{18})$aralkyl, or $(C_7-C_{18})$alkaryl, provided that aryl or the aryl portion of said aralkyl or alkaryl are optionally substituted with halo or methyl; and
$R_1$ is H, Cl or methyl.

Preferred compounds are those wherein R is selected from the group consisting of methyl, n-octyl, cyclohexyl, and 4-chlorophenyl.

Specific examples of each compound are (2-methyl-4-isothiazolin-3-on-5-yl)-(benzothiazol-2'-yl)sulfide, [4-chloro-2-(n-octyl)-4-isothiazolin-3-on-5-yl]-(benzothiazol-2'-yl)sulfide and [4-methyl-2-(4-chlorophenyl)-4-isothiazolin-3-on-5-yl]-(benzothiazole-2'-yl)sulfide.

Compositions comprising an effective amount of a compound of formula II with an agronomically acceptable carrier are useful to inhibit the growth of bacteria, fungi, algae, and the like.

The methods of application include incorporating the compound or composition comprising the compound into or onto a locus subject to contamination by fungi, algae, or bacteria.

The locus can be an aqueous medium. Preferably the compound (or a salt thereof) is incorporated in an amount of about 0.1 to 10,000 ppm by weight.

The locus can be a cutting oil formulation comprising a cutting oil, water, and an emulsifying agent; a water cooling system; a solid protective film; fabric; leather; paper; wood; or laundry wash water.

As stated above, compositions comprising a compound according to formula I and either an agronomically acceptable carrier, a cosmetic agent, a cutting oil, a soap or synthetic detergent, a stabilizer, a film forming material, or the like have a wide range of utility for protecting against or controlling microorganisms from a wide variety of classes including fungus, bacteria, algae, viruses and yeasts. The preferred utilities of the compositions are to protect wood, paint, adhesive, glue, paper, textile, leather, plastics, cardboard, lubricants, cosmetics, food, caulking, feed and industrial cooling water from microorganisms.

The following lists specific industries and applications of the compounds of compositions:

| Industry | Application |
|---|---|
| Adhesives, sealants | adhesives |
| | caulks |
| | sealants |
| Agriculture/food chain | adjuvant preservation |
| | agricultural active ingredient |
| | agricultural chemical preservative |
| | agricultural formulations preservation |

-continued

| Industry | Application |
|---|---|
| | animal feed preservation |
| | dairy chemicals |
| | fertilizer preservation |
| | food preservation |
| | food processing chemicals |
| | grain preservation |
| | post-harvest produce protection |
| | sugar processing |
| | tobacco |
| Construction products | asphalt/concrete |
| | cement modifiers |
| | construction products |
| | roof mastics |
| | synthetic stucco |
| | wall mastics |
| | joint cement |
| Cosmetics and toiletries | cosmetics |
| | raw materials for cosmetics, toiletries |
| | toiletries |
| Disinfectants, antiseptics | antiseptic |
| | disinfectant |
| Emulsions, dispersions | aqueous dispersions |
| | dispersed pigments |
| | latex |
| | photographic emulsions |
| | pigment slurries |
| | polymer latices |
| Formulated household products | fabric softeners |
| | polishes |
| | waxes |
| | hand dish detergents |
| | raw materials |
| | liquid detergents |
| | hand soaps |
| Industrial processing, misc | electrodeposition paint, baths, rinses |
| | electrodeposition pre-treatment, post rinses |
| | industrial fluids preservation |
| | pasteurization baths |
| | process aid preservation |
| Industrial water treatment | air washers |
| | cooling towers |
| | cooling water |
| | water cooling |
| | preservation/treatment of wooden cooling tower slats and structural members |
| | can warmers |
| | brewery pasteurization |
| | closed loop water cooling systems |
| Laundry | household laundry products |
| | laundered goods |
| | laundry wash water |
| | sanitizers-laundry |
| Leather, leather products | leather and hide |
| | leather and hide products |
| Lubricants, hydraulic aids | automotive lubricants and fluids |
| | conveyor lubricants |
| | greases |
| | hydraulic fluids |
| | lubricants |
| Medical devices | diagnostic enzymes |
| | diagnostic kits |
| | medical devices |
| Metalworking & related app's | cutting fluids |
| | metal cleaning |
| | metalworking fluids |
| Odor control (active ingredient) | air conditioning |
| | animal bedding |
| | cat litter |
| | chemical toilet prep'ns |
| | deodorizers |
| | humidifiers |
| | industrial deodorants |
| | sanitary formulations |
| | toilet bowls |
| Paints and coatings coating | emulsions |

-continued

| Industry | Application |
|---|---|
| | paints |
| Paper and wood pulp, their products | absorbant materials or paper and wood pulp |
| | packaging materials of paper and wood pulp |
| | paper |
| | paper products |
| | paper treatment |
| | soap wrap |
| | wood pulp |
| | wood pulp products |
| Paper mill | paper mill slimicides |
| | pulp and paper slurries |
| Petroleum refining, fuels | aviation fuels (jet fuel, aviation gas) |
| | crude oils |
| | burner, diesel and turbine fuel oils |
| | coal slurries |
| | diesel fuel additives |
| | diesel fuels |
| | fuels |
| | gasoline |
| | heating oils |
| | hydrocarbons |
| | kerosene |
| | liquified petroleum gas |
| | petrochemical feedstocks |
| | petroleum products, storage, transportation and production |
| | recycled petroleum products |
| | residual fuel oils |
| | turbine oils |
| Photographic chemicals and process | photographic processing - wash water, rinses |
| | photoprocessing |
| | photoplate processing chemicals (developers, stabilizers etc) |
| Printing | fountain solutions (printing) |
| | ink components (pigments, resins, solvents, etc) |
| | inks |
| Sanitizers (active) | sanitizers |
| | sanitizers-dairy |
| | sanitizers-dental |
| | sanitizers-fermentation |
| | sanitizers-food preparation |
| | sanitizers-food processing |
| | sanitizers-medical |
| | sanitizers-rendering |
| | sanitizers-veterinary |
| Soaps, detergents, cleaners | cleaners |
| | detergents |
| | household cleaners |
| | industrial cleaners |
| | liquid soaps |
| | oil and grease remover |
| | powdered soaps |
| | raw materials for cleaning products |
| | soaps |
| | surfactants |
| Textiles, textile products | bonded fabrics |
| | burlap |
| | canvas |
| | canvas goods |
| | carpet backing |
| | carpets |
| | clothing |
| | coated fabrics |
| | curtains |
| | draperies |
| | engineering textiles |
| | fibers |
| | geotextiles |
| | goods made of textiles |
| | knitted fabrics |
| | nets |
| | nonwoven fabrics |
| | rope |
| | rugs |

| Industry | Application |
|---|---|
| | textile accessories |
| | textile products |
| | textiles |
| | upholstery |
| | woven fabrics |
| | yarn |
| Textile processing | dye fixatives |
| | dyes |
| | fiber lubricants |
| | hand modifiers |
| | sizes |
| | textile processing fluids |
| Therapeutic (active or preservative) | animal health/veterinary |
| | aquaculture |
| | dental |
| | human health |
| | pharmaceutical/therapeutic |
| Water purification | charcoal beds |
| | deionization resins |
| | filters |
| | membranes |
| | reverse osmosis membranes |
| | ultrafilters |
| | water purification |
| | water purification pipes, tubing |
| Wood applications | lazures (wood stains) |
| | wood |
| | wood products |
| Miscellaneous | alcohols |
| | bedding incorporating water or gels |
| | ceramic |
| | contact lens cases-leaching |
| | electronic circuitry |
| | electronics chemicals |
| | enzymes-food production |
| | enzymes |
| | enzymes-industrial |
| | gel cushions |
| | marine antifoulants |
| | mildewcides |
| | wood |
| | plastics |
| | laundry |
| | mining |
| | natural rubber latex |
| | oil field injection waters including enhanced recover injection fluids, drilling, fracturing and completion fluids |
| | pipes |
| | plastics |
| | polymer systems |
| | polymers and resins (synthetic and natural) |
| | reagent preservation |
| | rubber |
| | rubber products |
| | skin remover |
| | solid protective/decorative films |
| | stains |
| | swimming pools |
| | waste treatment |
| | water beds |

The amounts of the compound to be used depend on the application. The useful amounts for a particular application are similar to amounts used for other microbicide compounds.

The compound can be used in combination with other microbicides. The term "microbicide" is considered equivalent to "antimicrobial" as used herein.

Suitable methods of application of compounds of formula II to control fungi, bacteria, algae, viruses, yeasts, and the like are in amounts and with carriers, etc., as well known in the art.

TABLE 1
Structure and Physical Data of Representative Compounds of Formula II

| Compound No. | R | $R_1$ | Melting Point |
|---|---|---|---|
| 1 | $CH_3$ | H | 143.0–145.0° C. |
| 2 | n-octyl | Cl | 78.0–80.0° C. |
| 3 | 4-chlorophenyl | $CH_3$ | 180–182.5° C. |

The compounds of formula II may be prepared according to Scheme 1. The 5-chloro-3-isothiazolone derivative is allowed to undergo nucleophilic substitution at the 5-position with sodium 2-mercaptobenzothiazole in aqueous ethanol solution to give compounds of formula II. The reaction takes place at room temperature, under alkaline condition (pH=8–10) and is complete within 1–96 hours.

The compounds may also be prepared in an anhydrous organic solvent as follows: 2-mercaptobenzothiazole is treated with sodium hydride in an anhydrous solvent such as dimethyl formamide or acetonitrile at 0° C. under nitrogen. Then a solution of 5-chloro-3-isothiazolone derivative in the same solvent is added. The mixture is allowed to warm to room temperature and then stirred for 1–24 hours to complete the reaction. The product precipitates out of solution or is obtained by extraction.

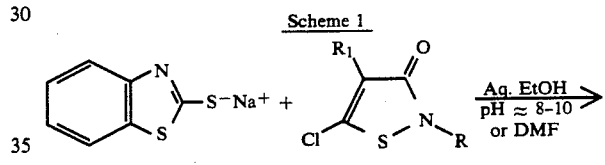

Scheme 1

R = Alkyl, aryl, substituted aryl
$R_1$ = H, Cl, alkyl

Compound 3 (R=4-chlorophenyl, $R_1$=$CH_3$) may be prepared from the acrylamide derivative III (Scheme 2). Treatment of an ethanol solution of III with 50% aqueous solution of sodium 2-mercaptobenzothiazole at pH 8–10 at room temperature yielded the product. The reaction takes place within 1–48 hours.

The acrylamide derivative III is postulated to initially undergo a rapid ring-closure initially under the basic reaction medium (pH 8–10) to give the isothiazolone derivative. Subsequently, the reaction follows scheme 1 to give the product.

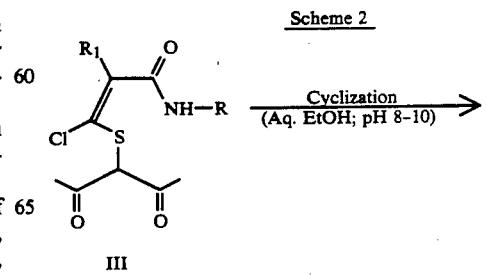

Scheme 2

III

-continued
Scheme 2

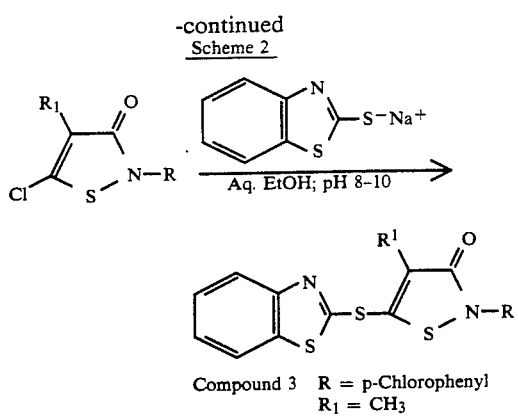

Compound 3  R = p-Chlorophenyl
R₁ = CH₃

The following examples are presented to illustrate a few embodiments of the invention. All parts and percentages are by weight unless otherwise indicated.

EXAMPLE 1

(2-methyl-4-isothiazolin-3-on-5-yl)-benzothiazol-2'-yl) sulfide (Compound 1)

To a solution of 5-chloro-2-methyl-4-isothiazolin-3-one (1 g, 0.0067 mol) in 25 ml of ethanol, 2 g of 50% aqueous solution of sodium 2-mercaptobenzothiazole was added. The resulting solution was adjusted to pH 8.5. The reaction mixture was allowed to stand at room temperature for 24 hours. The solid precipitate which formed was removed by filtration, washed with fresh water, followed by cold ethanol and then dried to give 0.9 g of the desired product. The compound was recrystallized from ethanol; m.p. 143.0°–145.0° C.

$^1$H-NMR (CDCl$_3$) δ7.3–8.1 (m 4H, arom.); 6.4 (s,1H, vinyl); 3.4 (s,3H,N-CH$_3$). IR (KBr) 1630 cm$^{-1}$.

EXAMPLE 2

[4-methyl-2-(4-chlorophenyl)-4-isothiazolin-3-on-5-yl]-(benzothiazol-2'-yl)sulfide (Compound 3)

To a stirred suspension of sodium hydride (60% dispersion in oil, 0.4 g, 0.01 mole) in 10 ml of dimethylformamide at 0° C. and under nitrogen, a solution of 2-mercaptobenzothiazole (1.67 g, 0.01 mole) in 10 ml of dimethylformamide was added dropwise. After stirring the mixture for 15 minutes at 0° C., a solution of 5-chloro-4-methyl-2-(4-chlorophenyl)-4-isothiazolin-3-one (2.6 g, 0.01 mole) in 10 ml of dimethylformamide was added dropwise. The mixture was allowed to warm up to room temperature and stirred for 2 hours. The precipitate which formed was removed by filtration and washed with ether. The solid was dried to give 3.2 g of product. The solid was recrystallized from chloroform/methanol solution; mp 180°–182.5° C. IR(KBr) 1635 cm$^{-1}$. $^1$H-NMR(CDCl$_3$) δ2.15 (s,3H,CH$_3$); 7.35–8.0 (m, 8H, Arom).

EXAMPLE 3

[4-methyl-2-(4-chlorophenyl)-4-isothiazolin-3-on-5-yl]-(benzothiazol-2'-yl)sulfide (Compound 3)

To a stirred 50% aqueous solution of sodium 2-mercaptobenzothiazole (0.53 g, 0.0014 mol) diluted with 10 ml of water, a solution of 4-chlorophenyl-2-methyl-3-chloro-3-thio (1-acetylpropan-2-on-1-yl) acrylamide (0.5 g, 0.0014 mol) in 15 ml of ethanol was added dropwise at room temperature. Stirring was continued for 2 hours. The precipitate which formed was removed by filtration, washed with water and then dried to give 0.57 g of product. The solid was recrystallized from chloroform/methanol solution to give pale-yellow compounds; mp 180°–182.5° C.; IR (KBr) 1635 cm$^{-1}$. $^1$NMR (CDCl$_3$) δ2.15 (s,3H,CH$_3$); 7.35–8.0 (m, 8H, Arom).

EXAMPLE 4

Biological Activity

Efficacy tests against eight fungi and four bacteria was carried out. A minimum inhibitory concentration (MIC) value was obtained using Trypticase Soy Broth, pH 7.0, and by preparing serial dilutions with a starting concentration of 500 ppm. A stock solution of the test compound was made in dimethyl sulfoxide (DMSO) or acetone.

The test organisms used to demonstrate biocidal activity are listed in Table 2. The MIC's of the compounds of this invention against the test organisms are shown in Table 3.

TABLE 2

| Microorganisms used in the Biocide Test | |
|---|---|
| Name | Abbreviations Used |
| Bacteria | |
| 1. Pseudomonas aeruginosa | Psae |
| 2. Staphylococcus aureus | Saur |
| 3. Escherichia coli | Ecol |
| 4. Pseudomonas fluorescens | Psfl |
| Fungi | |
| 1. Aspergillus niger | Anig |
| 2. Penicillium funiculosum | Pfun |
| 3. Cladosporium resinae | Cres |
| 4. Aureobasidium pullulans | Apul |
| 5. Chaetomium globosum | Cglo |
| 6. Saccharomyces cerevisiae | Scer |
| 7. Rhodotorula rubra | Rrub |
| 8. Gleophyllum trabeum | Gtra |

TABLE 3

MIC Test Data in PPM
Test was run in Trypticase Soy Broth, pH 7.0 Starting concentration = 500 pm

| Compound No. | A. nig | P. fun | C. res | A. pul | C. glo | G. tra | S. cer | R. rub | Ps. fl | Ps. ae | E. col | S. aur | Chorella |
|---|---|---|---|---|---|---|---|---|---|---|---|---|---|
| 1 | 8 | 8 | 1 | 16 | 32 | <0.1 | 8 | 16 | 8 | >500 | 500 | 4 | |
| 2 | 63 | | | 32 | | | | | | >250 | >250 | 1 | 4 |
| 3 | 12.5 | | | | | | | | 0.4 | 12.5 | | | |

While the invention has been described with reference to specific examples and applications, other modifications and uses for the invention will be apparent to those skilled in the art without departing from the spirit and scope of the invention defined in the appended claims.

I claim:

1. Compound or salt thereof having the formula

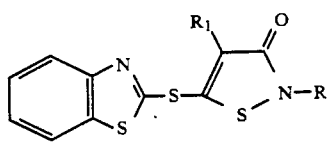

(II)

wherein
R is $(C_1-C_{18})$alkyl, $(C_3-C_8)$cycloalkyl, $(C_6-C_{18})$aryl, $(C_7-C_{18})$aralkyl, or $(C_7-C_{18})$alkaryl,
provided that aryl or the aryl portion of said aralkyl or alkaryl are optionally substituted with halo or methyl; and
$R_1$ is H, Cl or methyl.

2. Compound according to claim 1 wherein R is selected from the group consisting of methyl, n-octyl, cyclohexyl, and 4-chlorophenyl.

3. Compound according to claim 1 wherein said compound is selected from the group consisting of (2-methyl-4-isothiazolin-3-on-5-yl)-(benzothiazol-2'-yl)sulfide, [4-chloro-2-(n-octyl)-4-isothiazolin-3-on-5-yl]-(benzothiazol-2'-yl)sulfide and [4-methyl-2-(4-chlorophenyl)-4-isothiazolin-3-on-5-yl]-(benzothiazole-2'-yl)sulfide.

4. Composition for inhibiting the growth of bacteria, fungi, or algae comprising an effective amount of a compound according to claim 1 and an agronomically acceptable carrier.

5. Method for inhibiting the growth of bacteria, fungi, or algae in a locus subject to contamination by bacteria, fungi or algae which comprises incorporating onto or into the locus an amount which is effective to adversely affect the growth of bacteria, fungi or algae of a compound according to claim 1.

6. Method of claim 5 wherein the locus is an aqueous medium.

7. Method of claim 6 wherein the compound or salt thereof is incorporated in an amount of 0.1 to 10,000 ppm parts by weight.

8. Method of claim 5 wherein the locus is a cutting oil formulation comprising a cutting oil, water, and an emulsifying agent.

9. Method of claim 5 wherein the locus is water cooling system.

10. Method of claim 5 wherein the locus is a solid protective or decorative film.

11. Method of claim 5 wherein the locus is a fabric, leather, paper or wood.

12. Method of claim 5 wherein the locus is laundry wash water.

13. Method of claim 5 comprising contacting the bacteria, fungi or algae with said compound.

* * * * *